(12) United States Patent
Chen et al.

(10) Patent No.: US 8,378,143 B2
(45) Date of Patent: Feb. 19, 2013

(54) METHODS OF MAKING EFAVIRENS AND INTERMEDIATES THEREOF

(75) Inventors: Bo Chen, Qianjiang (CN); Zhi-Xian Wang, Tianjin (CN); Yutao Xue, Jinan (CN); Lihong Liu, Tangshan (CN); Hao Chen, Tian Jin (CN)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 13/330,381

(22) Filed: Dec. 19, 2011

(65) Prior Publication Data

US 2012/0095249 A1    Apr. 19, 2012

Related U.S. Application Data

(62) Division of application No. 12/505,627, filed on Jul. 20, 2009, now Pat. No. 8,080,655.

(51) Int. Cl.
*C07C 233/54* (2006.01)
(52) U.S. Cl. ...................................................... 564/218
(58) Field of Classification Search .................. 564/218
See application file for complete search history.

(56) References Cited

PUBLICATIONS

Chen et al., "Chemical Process Evolution of Efavirenz, a Potent Non-Nucleosidal HIV Reverse Transcriptase Inhibitor", Enantiomer, (1999), 4(6), 599-608.
Choudhury et al., "In Situ Recycling of Chrial Ligand and Surplus Nucleophile for a Noncatalytic Reaction: Amplification of Process Throughput in the Asymmetric Addition Step of Efavirens (DMP 266)", Organic Process Research & Development, (2003), 7(3), 324-328.
Choudhury et al., "Oxidative Removal of p-methyl-oxybenzyl-amino Protecting Group in the Presence of a Proximal Hydroxy Function: A Solution to a Process Problem in Sustiva(R) (Efavirenz) Synthesis", Synthetic Communications, (2001), 31(23), 3707-3714.
Jiang et al., "alpha-(Trifluoromethyl)ethenyl Boronic Acid as a Useful Trifluoromethyl Containing Building Block. Preparation and Palladium-Catalysed Coupling with Aryl Halides", Tetrahedron Letters, (2001), 42(24), 4083-4085.
Markwalder et al., "Synthesis and Biological Activities of Protential Metabolites of the Non-Nucleoside Reverse Transcriptase Inhibitor Efavirenz", Bioorganic & Medicinal Chemistry Letters, (2001), 11(5), 619-622.
Pedersen et al., "The Flourishing Synthesis of Non-Nucleoside Reverse Transcriptase Inhibitors", Synthesis, (2000), (4), 479-495.
Radesca et al., "Synthesis of HIV-1 Reverse Transcriptase Inhibitor DMP 266", Synthetic Communications, (1997), 27(24), 4373-4384.

*Primary Examiner* — Brian McDowell

(57) ABSTRACT

The present invention provides a process for the preparation of Efavirenz. A compound of Formula 1:

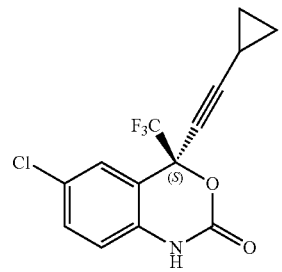

may be prepared by a process comprising cyclizing, in the presence of a first base, a compound of Formula 5 with a haloformate of Formula 6. Other processes are also provided as well as novel compounds prepared by and used in such processes.

7 Claims, No Drawings

METHODS OF MAKING EFAVIRENS AND INTERMEDIATES THEREOF

RELATED APPLICATIONS

This application is a divisional application of U.S. patent application Ser. No. 12/505,627, filed Jul. 20, 2009, now U.S. Pat. No. 8,080,655.

TECHNICAL FIELD

This invention relates to the field of chemical synthesis of organic compounds and in particular to a synthesis of Efavirenz and intermediates thereof.

BACKGROUND

A common feature of retrovirus replication is reverse transcription of the RNA genome by a virally encoded reverse transcriptase to generate DNA copies of human immunodeficiency virus (HIV) sequences. Therefore, reverse transcriptase is a clinically relevant target for the chemotherapy of retroviral infections.

It is known that a number of benzoxazinone compounds are effective in the treatment of HIV which is the retrovirus that causes progressive destruction of the human immune system with the resultant onset of AIDS. Among them, the (S)-6-chloro-4-cyclopropylethynyl-4-trifluoromethyl-1,4-dihydro-2H-3,1-benzoxazin-2-one of Formula 1 (Efavirenz) is not only a highly potent reverse transcriptase inhibitor, but also efficacious against HIV reverse transcriptase resistance.

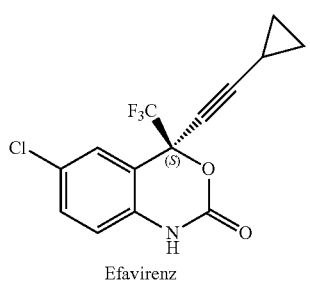

Efavirenz (1)

U.S. Pat. No. 5,519,021 discloses certain benzoxazinones that are useful in the inhibition of HIV reverse transcriptase (including its resistant varieties), the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

In U.S. Pat. No. 5,633,405 an improved synthesis of a highly potent HIV reverse transcription inhibitor is disclosed, involving an acetylide and a trifluoromethyl ketone which produces a chiral product in the presence of a chiral amino alcohol. See also *Tetrahedron Lett.* 1995, 36, 8937 and *J. Org. Chem.* 1998, 63, 8536.

U.S. Pat. No. 5,922,864 discloses an efficient method for the preparation of a compound of (−)-6-chloro-4-cyclopropylethynyl-4-trifluoromethyl-1,4-dihydro-2H-3, 1-benzoxazin-2-one, also known as DMP-266, a reverse transcriptase inhibitor using a cyclization reaction of the amino alcohol intermediate with an alkyl or aryl chloroformate and a base.

U.S. Pat. No. 5,925,789 provides novel methods for the asymmetric synthesis of (S)-6-chloro-4-cyclopropylethynyl-4-trifluoromethyl-1,4-dihydro-2H-3,1-benzoxazin-2-one of Formula 1 which is useful as a human immunodeficiency virus (HIV) reverse transcriptase inhibitor.

U.S. Pat. No. 5,952,528 discloses a process for enhancing the purity of 2R-[1-hydroxy-1-trifluoromethyl-3-cyclopropylpropyn-2-yl]-4-chloroaniline comprising the formation of an acid addition salt which is capable of rejecting the racemate in the selected organic solvent.

U.S. Pat. No. 6,015,926 discloses an efficient method for the preparation of key intermediate, in the synthesis of (−)-6-chloro-4-cyclopropylethynyl-4-trifluoromethyl-1,4-dihydro-2H-3,1-benzoxazin-2-one, a reverse transcriptase inhibitor is achieved using a chiral addition reaction to the 4-chloro-2-trifluoromethylketoaniline with an organozinc complex to give the desired alcohol. This instant method has broad applicability in the chiral addition to any prochiral ketone.

U.S. Pat. No. 7,205,402 provides novel methods for the synthesis of (S)-6-chloro-4-cyclopropylethynyl-4-trifluoromethyl-1,4-dihydro-2H-3,1-benzoxazin-2-one of Formula 1 which is useful as a human immunodeficiency virus (HIV) reverse transcriptase inhibitor.

U.S. Pat. No. 7,439,400 disclosed a new process of asymmetric alkynylation of ketone or ketimine, involving the chiral ligand-mediated asymmetric addition of zinc or copper acetylide to a trifluoromethyl ketone or ketimine intermediate to give a chiral tertiary propargylic alcohols or amines. The adduct compounds include the key precursors to the potent HIV reverse transcriptase inhibitor Efavirenz (DMP 266), DPC 961 and DPC 083. The invention also disclosed a novel chiral amino ligand.

SUMMARY

The present invention is directed to methods of preparation of Efavirenz, various intermediates useful in the preparation of Efavirenz and methods of preparation of such intermediates.

In some embodiments, the present invention allows for removal of the aniline auxiliary group of a compound of Formula 5 during the cyclization step without additional chemical reagent or treatment.

In some embodiments, the stereoselectivity of the cyclopropylacetylide reaction may be controlled by introduction of an appropriate chiral carbonyl auxiliary group on the aniline nitrogen. The product of such an asymmetric addition may then undergo a cyclization reaction with concomitant removal of the chiral auxiliary group, without the need for a discrete deprotection step.

In illustrative embodiments of the present invention there is provided a process for the preparation of a compound of Formula 1:

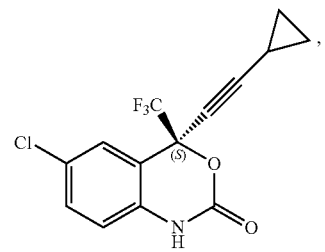

the process comprising cyclizing, in the presence of a first base, a compound of Formula 5:

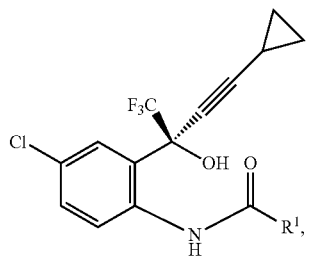

with a haloformate of Formula 6:

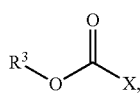

wherein $R^1$ is alkyl, substituted alkyl, aryl, substituted aryl, arylalkyl, substituted arylalkyl or a chiral auxiliary group; $R^3$ is alkyl, substituted alkyl, aryl, substituted aryl, arylalkyl, or substituted arylalkyl; and X is halogen.

In illustrative embodiments of the present invention there is provided a process described herein further comprising treatment with a second base.

In illustrative embodiments of the present invention there is provided a process described herein wherein an intermediate of Formula 7:

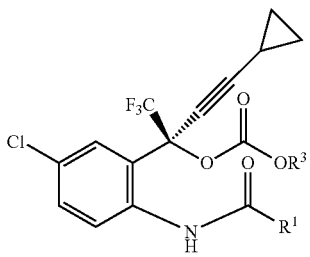

is isolated before treatment with the second base, wherein $R^1$ is alkyl, substituted alkyl, aryl, substituted aryl, arylalkyl, substituted arylalkyl or a chiral auxiliary group; and $R^3$ is alkyl, substituted alkyl, aryl, substituted aryl, arylalkyl, or substituted arylalkyl.

In illustrative embodiments of the present invention there is provided a process described herein wherein the second base is selected from the group consisting of sodium hydroxide, potassium hydroxide, lithium hydroxide, sodium carbonate, potassium carbonate, lithium carbonate, triethylamine diisopropylethylamine, N,N-dimethylaniline, and N,N-diethylaniline, pyridine and mixtures thereof.

In illustrative embodiments of the present invention there is provided a process described herein wherein $R^1$ is selected from the group consisting of methyl, ethyl, isobutyl, tert-butyl, and benzyl.

In illustrative embodiments of the present invention there is provided a process described herein wherein $R^1$ is a chiral auxiliary group.

In illustrative embodiments of the present invention there is provided a process described herein wherein the compound of Formula 5 is (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide.

In illustrative embodiments of the present invention there is provided a process described herein wherein the compound of Formula 5 is (R)-2-(4-chloro-2-((S)-4-cyclopropyl-1,1,1-trifluoro-2-hydroxybut-3-yn-2-yl)phenylamino)-2-oxo-1-phenylethyl pivalate.

In illustrative embodiments of the present invention there is provided a process described herein wherein the haloformate of Formula 6 is selected from the group consisting of 4-nitrophenyl haloformate, 4-chlorophenyl haloformate, phenyl haloformate and 1-chloroethyl haloformate.

In illustrative embodiments of the present invention there is provided a process described herein wherein the first base is selected from the group consisting of sodium hydroxide, potassium hydroxide, lithium hydroxide, sodium carbonate, potassium carbonate, lithium carbonate, triethylamine diisopropylethylamine, N,N-dimethylaniline, and N,N-diethylaniline, pyridine and mixtures thereof.

In illustrative embodiments of the present invention there is provided a process for making a compound of Formula 5:

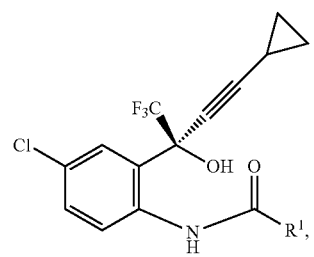

the process comprising: i) reacting a compound of Formula 2:

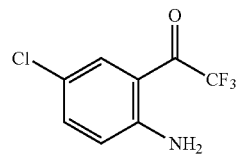

or an acid addition salt thereof, with a chiral acylating agent of Formula $R^2COG$ to form a compound of Formula 3, Formula 3a or a mixture thereof:

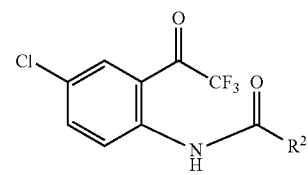

-continued

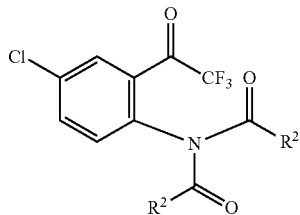

ii) reacting the compound of Formula 3, Formula 3a or the mixture thereof with a compound of Formula 4:

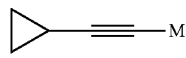

to form the compound of Formula 5, wherein $R^2$ is a chiral auxiliary group; G is a hydroxyl group, or a leaving group; and M is a metal.

In illustrative embodiments of the present invention there is provided a process described herein wherein G is chloro or the hydroxyl group and $R^2$ is:

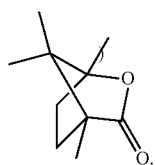

In illustrative embodiments of the present invention there is provided a process described herein wherein G is chloro and $R^2$ is:

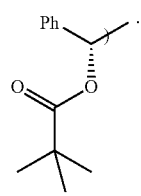

In illustrative embodiments of the present invention there is provided a process described herein wherein $R^2$ is:

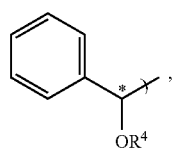

$R^4$ is a hydroxyl protecting group; and the carbon center designated "*" is enantiomerically enriched in a (R)- or (S)-configuration.

In illustrative embodiments of the present invention there is provided a process described herein wherein M is lithium, sodium, potassium, magnesium halide or mixtures thereof.

In illustrative embodiments of the present invention there is provided a process described herein wherein M is lithium.

In illustrative embodiments of the present invention there is provided a process for the preparation of a compound of Formula 1:

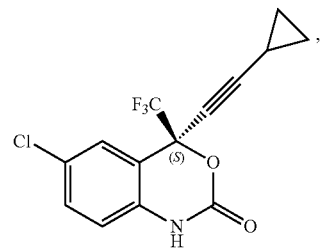

the process comprising: i) reacting a compound of Formula 2:

or an acid addition salt thereof, with a chiral acylating agent of Formula $R^2COG$ to form a compound of Formula 3, Formula 3a or a mixture thereof:

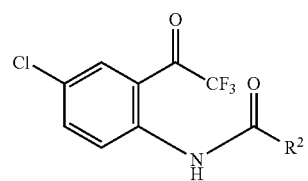

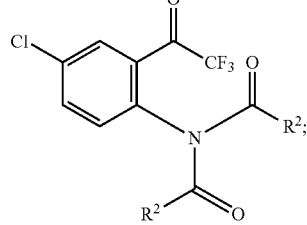

ii) reacting the compound of Formula 3, Formula 3a or the mixture thereof with a compound of Formula 4:

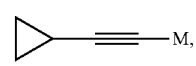

to form a compound of Formula 5:

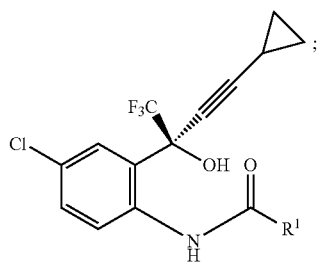

iii) hydrolysing the compound of Formula 5 to form a compound of Formula 8:

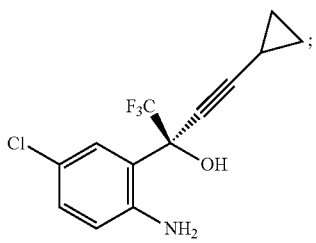

and iv) cyclizing the compound of Formula 8 to give the compound of Formula 1, wherein $R^1$ and $R^2$ are a chiral auxiliary group; G is a hydroxyl group, or a leaving group; and M is a metal.

In illustrative embodiments of the present invention there is provided a process described herein wherein G is chloro or the hydroxyl group and $R^1$ and $R^2$ are:

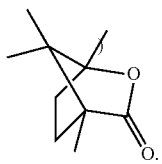

In illustrative embodiments of the present invention there is provided a process described herein wherein G is chloro and $R^1$ and $R^2$ are:

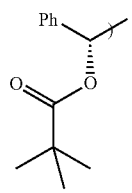

In illustrative embodiments of the present invention there is provided a process described herein wherein $R^1$ and $R^2$ are:

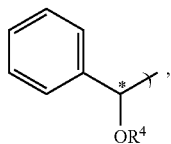

$R^4$ is a hydroxyl protecting group; and the carbon centre designated "*" is enantiomerically enriched in a (R)- or (S)-configuration.

In illustrative embodiments of the present invention there is provided a process described herein wherein M is lithium, sodium, potassium, magnesium halide or a mixture thereof.

In illustrative embodiments of the present invention there is provided a process described herein wherein M is lithium.

In illustrative embodiments of the present invention there is provided a process described herein wherein the cyclization of a compound of Formula 8 to give the compound of Formula 1 is performed with a cyclization reagent selected from the group consisting of $C_1$-$C_{10}$ alkyl haloformates, $C_6$-$C_{12}$ aryl haloformates, phosgene, triphosgene and 1,1'-carbonyldiimidazole.

In illustrative embodiments of the present invention there is provided a compound of Formula 3:

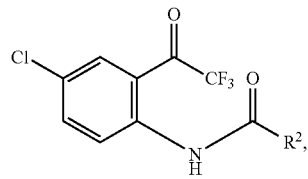

wherein $R^2$ is a chiral auxiliary group.

In illustrative embodiments of the present invention there is provided a compound of Formula 3a:

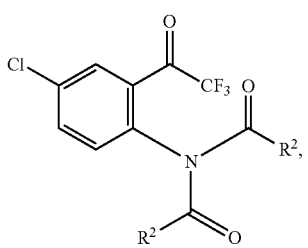

wherein $R^2$ is a chiral auxiliary group.

In illustrative embodiments of the present invention there is provided a compound of Formula 5:

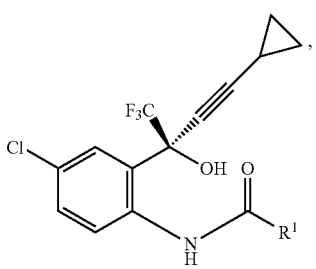

wherein $R^1$ is a chiral auxiliary group.

In illustrative embodiments of the present invention there is provided a process described herein wherein the chiral auxilliary group is Q of a chiral acid QCOOH, wherein QCOOH is selected from the group consisting of: natural chiral organic acids, natural chiral organic acid derivatives, unnatural chiral organic acids, unnatural chiral organic acid derivatives, natural amino acid derivatives, and unnatural amino acid derivatives.

In illustrative embodiments of the present invention there is provided a process described herein wherein the chiral auxiliary group is a chiral $C_1$-$C_{10}$ alkoxyl or a chiral $C_6$-$C_{12}$ aralkoxyl group.

In illustrative embodiments of the present invention there is provided a compound of Formula 9:

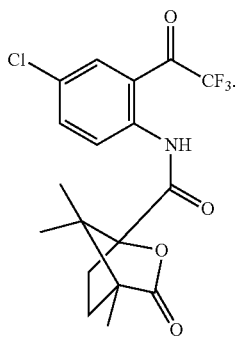

9

In illustrative embodiments of the present invention there is provided a compound of Formula 10:

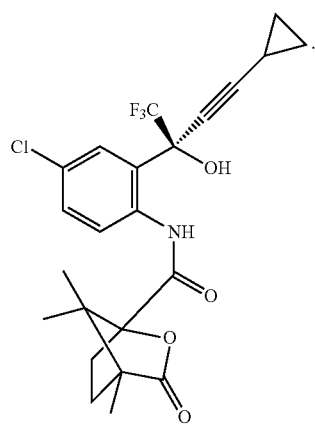

10

In illustrative embodiments of the present invention there is provided a compound of Formula 11:

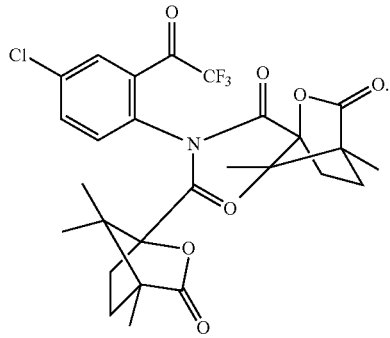

11

In illustrative embodiments of the present invention there is provided a compound of Formula 12:

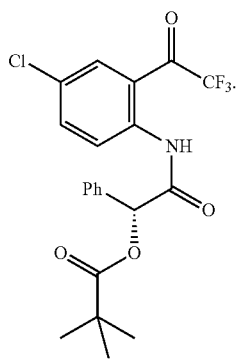

12

In illustrative embodiments of the present invention there is provided a compound of Formula 13:

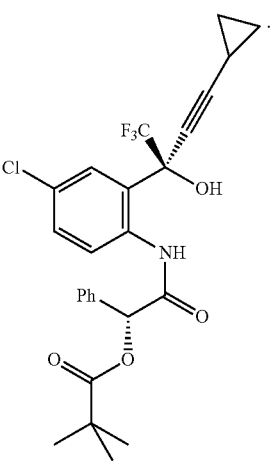

13

In illustrative embodiments of the present invention there is provided a compound of Formula 14:

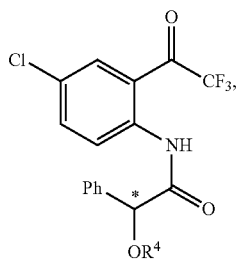

14 wherein $R^4$ is a hydroxyl protecting group; and the carbon centre designated "*" is enantiomerically enriched in a (R)- or (S)-configuration.

In illustrative embodiments of the present invention there is provided a compound of Formula 15:

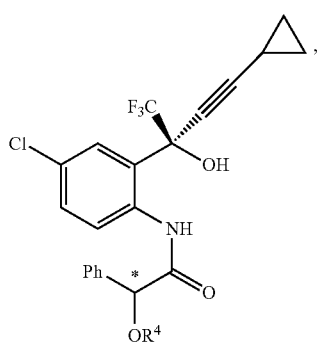

wherein R⁴ is a hydroxyl protecting group; and the carbon centre designated "*" is enantiomerically enriched in a (R)- or (S)-configuration.

In illustrative embodiments of the present invention there is provided a compound of Formula 7:

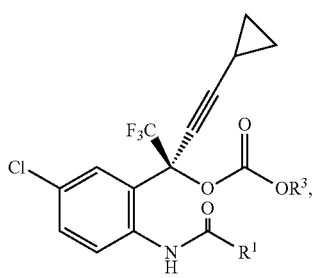

wherein R¹ is alkyl, substituted alkyl, aryl, substituted aryl, arylalkyl, substituted arylalkyl or a chiral auxiliary group; and R³ is alkyl, substituted alkyl, aryl, substituted aryl, arylalkyl, or substituted arylalkyl.

In illustrative embodiments of the present invention there is provided a composition comprising a compound of Formula 1:

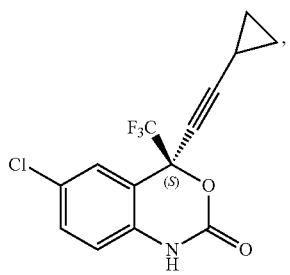

and a compound of Formula 7:

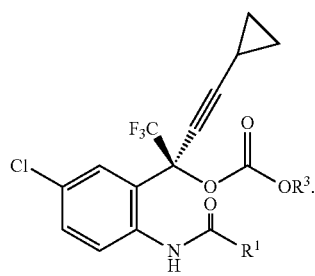

In illustrative embodiments of the present invention there is provided a composition comprising a compound of Formula 1:

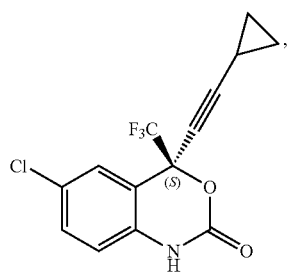

and a compound of Formula 5:

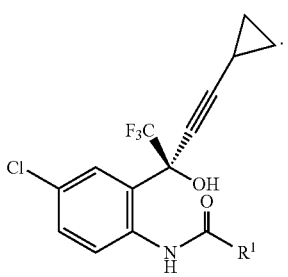

Other aspects and features of the present invention will become apparent to those ordinarily skilled in the art upon review of the following description of specific embodiments of the invention in conjunction with the accompanying figures.

DETAILED DESCRIPTION

As used herein, the term "substituted" refers to the replacement of a hydrogen atom on a compound with a substituent group. A substituent may be a non-hydrogen atom or multiple atoms of which at least one is a non-hydrogen atom and one or more may or may not be hydrogen atoms. For example, without limitation, substituted compounds may comprise one or more substituents selected from the group consisting of: R", OR", NR"R"', SR", halogen, SiR"R"'R"", OC(O)R", C(O)R", CO₂R", CONR"R"', NR"'C(O)₂R", S(O)R", S(O)₂R", CN and NO₂.

As used herein, each R", R"', and R"" may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

As used herein, the term "alkyl" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (e.g. C₁-C₁₀ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "aryl" by itself or as part of another substituent, means, unless otherwise stated, a polyunsaturated, aromatic, hydrocarbon substituent which can be a single ring or multiple rings (often from 1 to 3 rings) which are fused together or linked covalently. "Aryl" includes, but is not limited to, "heteroaryl" groups. "Heteroaryl" refers to an aryl group that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include: phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc).

As used herein the term "leaving group" refers to a halogen atom (e.g. chlorine, bromine and iodine) and/or sulfonyloxy groups (e.g. methanesulfonyloxy, trifluoromethanesulfonyloxy, p-toluenesulfonyloxy).

As used herein, the term "chiral auxiliary group" refers to any chiral chemical compound or unit that is temporarily incorporated into an organic synthesis for the purpose of altering the stereochemical outcome of a subsequent reaction. Chiral auxiliaries are optically active compounds and introduce chirality in otherwise racemic compounds. After it has served its purpose the chiral auxiliary can be removed in a later step and recycled.

As used herein, "hydroxyl protecting group" refers to a protecting group that is introduced into a molecule by chemical modification of a hydroxy group in order to obtain chemoselectivity in a subsequent chemical reaction. Such hydroxyl protecting groups include those listed in Greene, T. W. and Wuts, P. G. M., "Chapter 2, Protection for the hydroxyl group, including 1,2- and 1,3-diols", in "Protective Groups in Organic Synthesis", Fourth Edition, John Wiley & Sons, Inc., 2007, pp. 16-366. Hydroxyl protecting group includes, but is not limited to 1) ethers, including silyl ethers such as trimethylsilyl (TMS) ether, tert-butyldimethylsilyl (TBDMS) ether, and triisopropylsilyl (TIPS) ether, tetrahydropyran (THP), β-methoxyethoxymethyl ether (MEM), p-methoxybenzyl ether (PMB), methoxymethyl ether (MOM), ethoxyethyl ethers (EE), methyl ether, benzyl ether, methylthiomethyl ether; and 2) esters such as pivaloyl (Piv) esters.

According to illustrative embodiments of the present invention, there is provided a process for the preparation of a compound of Formula 1:

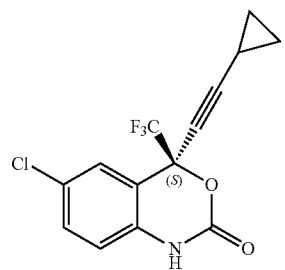

comprising cyclization, in the presence of a first base, of a compound of Formula 5:

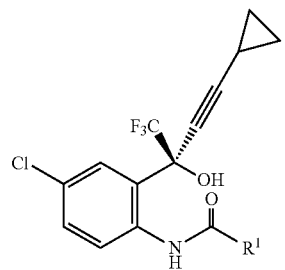

with a haloformate of Formula 6:

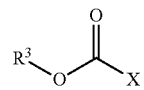

wherein
$R^1$ is $C_1$-$C_{10}$ alkyl, substituted $C_1$-$C_{10}$ alkyl, $C_6$-$C_{12}$ aryl, substituted $C_6$-$C_{12}$ aryl, $C_6$-$C_{12}$ arylalkyl, substituted $C_6$-$C_{12}$ arylalkyl or a chiral auxiliary group;
$R^3$ is $C_1$-$C_{10}$ alkyl, substituted $C_1$-$C_{10}$ alkyl, $C_6$-$C_{12}$ aryl, substituted $C_6$-$C_{12}$ aryl, $C_6$-$C_{12}$ arylalkyl, or substituted $C_6$-$C_{12}$ arylalkyl; and
X is halogen;
optionally followed by treatment with a second base.

In some embodiments of Formula 5, $R^1$ is selected from the group consisting of $C_1$-$C_{10}$ alkyl, substituted $C_1$-$C_{10}$ alkyl, $C_6$-$C_{12}$ aryl, substituted $C_6$-$C_{12}$ aryl, $C_6$-$C_{12}$ arylalkyl and substituted $C_6$-$C_{12}$ arylalkyl. In some embodiments of Formula 5, $R^1$ is selected from the group consisting of methyl, ethyl, propyl, isopropyl, butyl, isobutyl, tert-butyl, cyclopentyl, cyclohexyl, hexyl, phenyl, and benzyl. In some embodiments of Formula 5, $R^1$ is selected from the group consisting of methyl, ethyl, isobutyl, tert-butyl, and benzyl. In some embodiments of Formula 5, $R^1$ is a chiral auxiliary group. In some embodiments of Formula 5 the chiral auxiliary group is Q of a chiral acid QCOOH, wherein QCOOH is selected from natural chiral organic acids, natural chiral organic acid derivatives, unnatural chiral organic acids, unnatural chiral organic acid derivatives, natural amino acid derivatives, and unnatural amino acid derivatives. In some embodiments of Formula 5, $R^1$ is Q of a chiral acid QCOOH, wherein QCOOH is a chiral acid selected from the group consisting of camphanic acid, 2-pyrrolidone-5-carboxylic acid, naproxen, ibuprofen; tartaric acid, malic acid, lactic acid, 3-hydroxybutyric acid, mandelic acid or derivatives thereof. In other embodiments of Formula 5, the chiral auxiliary group is a chiral alkoxyl or chiral aralkoxyl group such as the menthoxy or camphanoxy groups:

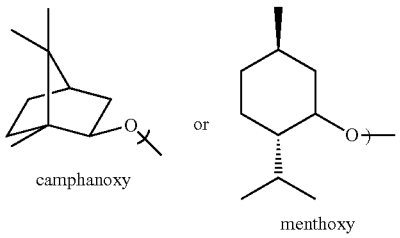

camphanoxy or menthoxy

In some embodiments of Formula 5 the chiral auxiliary group is one of the following two groups:

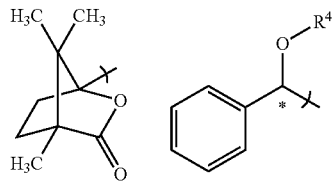

wherein $R^4$ is a hydroxyl protecting group, and the carbon centre designated "*" is enantiomerically enriched in a (R)- or (S)-configuration.

In some embodiments, the haloformate of Formula 6 is selected from the group consisting of $C_1$-$C_{10}$ alkyl haloformate, substituted $C_1$-$C_{10}$ alkyl haloformate, $C_6$-$C_{12}$ aryl haloformate, and substituted $C_6$-$C_{12}$ aryl haloformate. In some embodiments, the haloformate of Formula 6 is selected from the group consisting of methyl haloformate, ethyl haloformate, hydroxymethyl haloformate, hydroxyethyl haloformate, 1-chloroethyl haloformate, 2-chloroethyl haloformate, phenyl haloformate, hydroxyphenyl haloformate, dihydroxyphenyl haloformate, trihydroxyphenyl haloformate, methyoxyphenyl haloformate, chlorophenyl haloformate, dichlorophenyl haloformate, trichlorophenyl haloformate, pentachlorophenyl haloformate and 4-nitrophenyl haloformate. In some embodiments, the haloformate of Formula 6 is selected from the group consisting of 4-nitrophenyl haloformate, phenyl haloformate and 1-chloroethyl haloformate.

The first and second base may be the same or different. The first and/or second base may be any of a variety of bases which facilitates the desired reaction. The first and/or second base may be an organic or inorganic base. The first and/or second base may be selected from the group consisting of sodium hydroxide, potassium hydroxide, lithium hydroxide, sodium carbonate, potassium carbonate, lithium carbonate, triethylamine, diisopropylethylamine, N,N-dimethylaniline, N,N-diethylaniline, pyridine and mixtures thereof. The first and/or second base may be triethylamine, diisopropylamine, sodium hydroxide or potassium carbonate.

In some embodiments, the cyclization is a step-wise process, whereby the compound of Formula 5 is treated with the haloformate of Formula 6 in the presence of the first base to form an intermediate carbonate of Formula 7:

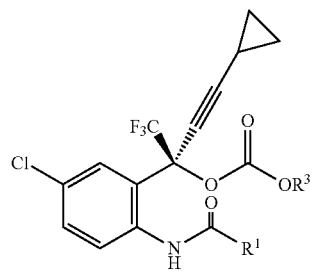

wherein $R^1$ may be as defined above for Formula 5 and $R^3$ may be as defined above for Formula 6. The intermediate carbonate of Formula 7 is subsequently treated with the second base to induce cyclization. The intermediate carbonate of Formula 7 may or may not be isolated before treatment with the second base. The isolation of the carbonate of Formula 7 also provides for an additional opportunity to purify and in some cases may provide for a purer product. In a step-wise process, the same solvent may be used throughout or a different solvent may be used for each step.

Since the same solvent may be used throughout, in some embodiments, the cyclization may also be carried out in a one-step and/or a one-pot process, whereby cyclization of the compound of Formula 5 occurs upon treatment with the haloformate in the presence of the first base. In some embodiments, the first base may be added in a portion wise process.

The cyclization may occur in a first solvent. The first solvent may be selected from group consisting of $C_1$-$C_{10}$ alkyl ethers (e.g. diethyl ether, methyl t-butyl ether, diisopropyl ether, butyl ether), $C_1$-$C_{10}$ alkyl esters (e.g. ethyl acetate), $C_1$-$C_{10}$ ketones (e.g. acetone, methyl ethyl ketone, methyl isobutyl ketone), $C_6$-$C_{12}$ aromatic hydrocarbons and $C_1$-$C_{10}$ aliphatic hydrocarbons (e.g. toluene, xylenes, hexanes and heptanes), $C_1$-$C_{12}$ nitriles, (e.g. acetonitrile, propionitrile, butyronitrile, and benzonitrile) $C_1$-$C_{12}$ N,N-dialkylamides (e.g. N,N-dimethylformamide, N,N-dimethylacetamide and N-methyl-2-pyrrolidinone), $C_1$-$C_{10}$ sulfoxides and $C_1$-$C_{10}$ sulfones (e.g. dimethyl sulfoxide and sulfolane), halogenated $C_1$-$C_{10}$ hydrocarbons (e.g. dichloromethane and dichloroethane), water and mixtures thereof. The first solvent may be toluene, dichloromethane, methyl t-butyl ether or N,N-dimethylformamide.

The compound of Formula 5, may be prepared by acylation of a compound of Formula 8:

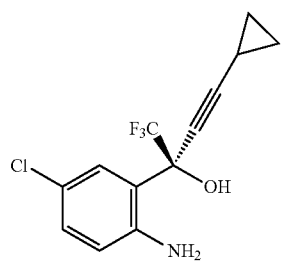

according to known methods in the art, for example, see Francis A. Carey and Richard J. Sundberg, "Advanced Organic Chemistry, Part B: Reactions and Synthesis", Fifth Edition, Springer, 2007, pages 252-258. The compound of Formula 8 may be prepared according to the method described in this invention or other methods known in the art.

According to illustrative embodiments of the present invention there is provided a process for the preparation of a compound of Formula 5 wherein $R^1$ is a chiral auxiliary group, the process comprising:

i) reacting a compound of Formula 2:

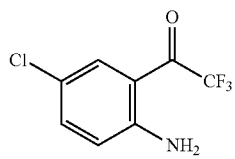
2 or an acid addition salt thereof, with a chiral acylating agent of Formula $R^2COG$ to form a compound of Formula 3, 3a or mixtures thereof:

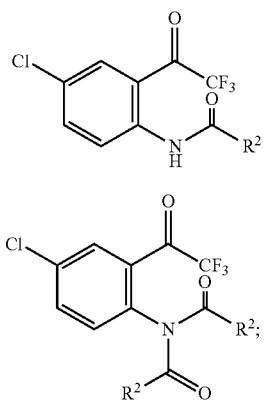
3

3a and ii) reacting the compound of Formula 3, 3a or mixtures thereof with a compound of Formula 4:

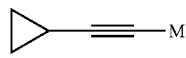
4 to give a compound of Formula 5,
wherein
$R^2$ is a chiral auxiliary group;
G is a hydroxyl group, or a leaving group; and
M is a metal.

In some embodiments of Formula 3 and/or 3a, $R^2$ is Q of a chiral acid QCOOH, wherein QCOOH is selected from natural chiral organic acids, natural chiral organic acid derivatives, unnatural chiral organic acids, unnatural chiral organic acid derivatives, natural amino acid derivatives, and unnatural amino acid derivatives. In other embodiments of Formula 3 and/or 3a, the chiral auxiliary group is a chiral alkoxyl or chiral aralkoxyl group such as the menthoxy or camphanoxy group. In some embodiments of Formula 3 and/or 3a, $R^2$ is Q of a chiral acid QCOOH, wherein QCOOH is a chiral acid selected from the group consisting of camphanic acid, 2-pyrrolidone-5-carboxylic acid, naproxen, ibuprofen; tartaric acid, malic acid, lactic acid, 3-hydroxybutyric acid, mandelic acid and derivatives thereof. In some embodiments of Formula 3 and/or 3a, $R^2$ is one of the following two groups:

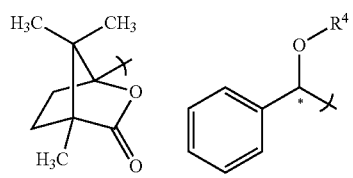

wherein $R^4$ is a hydroxyl protecting group, and the carbon centre designated "*" is enantiomerically enriched in a (R)- or (S)-configuration.

The leaving group G may be independently selected from the group consisting of: halogen atoms (e.g. chlorine, bromine and iodine) and sulfonyloxy groups (e.g. methanesulfonyloxy, trifluoromethanesulfonyloxy, p-toluenesulfonyloxy). In some embodiments, G is chlorine.

The chiral acylating agent of Formula $R^2COG$ may be (−)-camphanic acid, (−)-camphanoyl chloride, or (R)-2-chloro-2-oxo-1-phenethyl pivalate.

The reaction of the compound of Formula 2 and the chiral acylating agent may occur in the presence of a third base in a second solvent. The third base may be any of a variety of bases which facilitates the desired reaction. The third base may be organic or inorganic. The third base may be selected from the group consisting of sodium hydroxide, potassium hydroxide, lithium hydroxide, sodium carbonate, potassium carbonate, lithium carbonate, triethylamine, diisopropylethylamine, N,N-dimethlyaniline, N,N-diethylaniline, pyridine, and mixtures thereof.

In some embodiments, when G is a hydroxyl group, the reaction of the compound of Formula 2 and the chiral acylating agent may occur in the presence of an acid catalyst in the second solvent. The acid catalyst may be organic or inorganic. The acid catalyst may be selected from the group consisting of sulfuric acid, hydrogen chloride, p-toluenesulfonic acid, benzenesulfonic acid, and mixtures thereof.

The second solvent may be selected from the group consisting of $C_1$-$C_{10}$ alkyl ethers (e.g. diethyl ether, methyl t-butyl ether, diisopropyl ether, butyl ether), $C_1$-$C_{10}$ alkyl esters (e.g. ethyl acetate), $C_1$-$C_{10}$ ketones (e.g. acetone, methyl ethyl ketone, methyl isobutyl ketone), aromatic $C_6$-$C_{12}$ hydrocarbons and aliphatic $C_1$-$C_{10}$ hydrocarbons (e.g. toluene, xylenes, hexanes and heptanes), $C_1$-$C_{10}$ nitriles, (e.g. acetonitile, propionitrile, butyronitrile, and benzonitrile) $C_1$-$C_{12}$ N,N-dialkylamides (e.g. N,N-dimethylformamide, N,N-dimethylacetamide and N-methyl-2-pyrrolidinone), $C_1$-$C_{10}$ sulfoxides and $C_1$-$C_{10}$ sulfones (e.g. dimethyl sulfoxide and sulfolane), halogenated $C_1$-$C_{10}$ hydrocarbons (e.g. dichloromethane and dichloroethane), water and mixtures thereof. The second solvent may be dichloromethane.

The metal may be a salt of a divalent cation, such as $Zn^{2+}$ or $Mg^{2+}$, or a monovalent cation, such as $Li^+$, $Na^+$ or $K^+$. The cyclopropyl acetylide metal reagent may be prepared in situ from the reaction of cyclopropyl acetylene and an organometallic compound. The organometallic compound may be selected from the group consisting of organomagnesium, organozinc, organosodium, organolithium compounds and mixtures thereof. The organometallic compound may be selected from the group consisting of alkylmagnesium halide, alkylzinc halide, alkyllithium, lithium hexaalkyldisilazide, sodium hexaalkyldisilazide, and potassium hexaalkyldisilazide. The organometallic compound may be selected from the group consisting of ethylmagnesium chloride, methylmagnesium chloride, n-butyllithium, sec-butyllithium, tert-butyllithium, n-hexyllithium and lithium hexamelthyldisilazide.

The reaction of a compound of Formula 3 and/or 3a with a compound of Formula 4 may be done in the presence of a third solvent. The third solvent may be an aprotic solvent. The third solvent may be an $C_1$-$C_{10}$ alkyl ether. The third solvent may be tetrahydrofuran.

The reaction may be done at a temperature range between about $-78°$ C. to about $30°$ C., In some embodiments, reaction of a compound of Formula 3 and/or 3a with a compound of Formula 4 may give a mixture of two diastereomers of the Formula 5 and 5a:

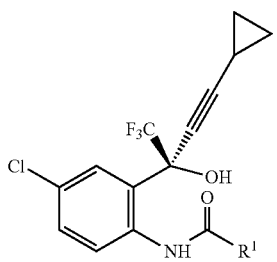

5

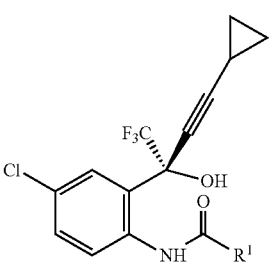

5a wherein a desired isomer of the compound of Formula 5 is a major product and $R^1$ is a chiral auxiliary group. The ratio between the 5 (S) and 5a (R) isomers may range from about 1.1:1 to >99:1. The desired isomer can then be isolated using typical separation methods including selective crystallization.

According to illustrative embodiments of the present invention there is provided a process for the preparation of the compound of Formula 1:

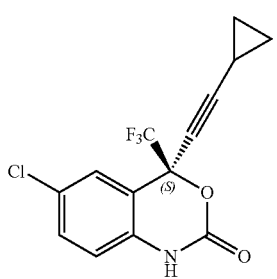

1 the process comprising:

i) reacting a compound of Formula 2:

2 or an acid addition salt thereof, with a chiral acylating agent of Formula $R^2COG$ to form a compound of Formula 3, 3a or mixtures thereof:

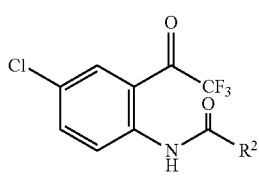

3

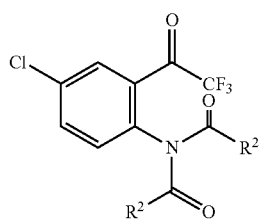

3a ii) reacting the compound of Formula 3, 3a or mixtures thereof with a compound of Formula 4:

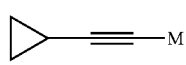

4 to give a compound of Formula 5:

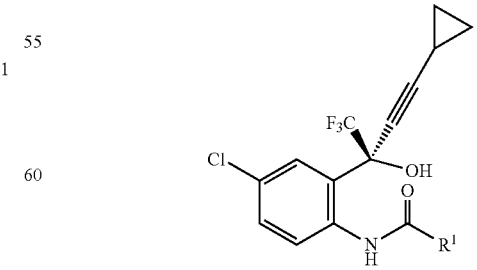

5 iii) hydrolysing the compound of Formula 5 to form a compound of Formula 8:

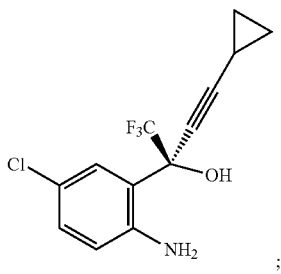

and;
iv) cyclizing the compound of Formula 8 to give the compound of Formula 1,
wherein
R¹ is a chiral auxiliary group;
R² is a chiral auxiliary group;
G is a hydroxyl group, or a leaving group; and
M is a metal.

In some embodiments of Formula 3 and/or 3a, R² is Q of a chiral acid QCOOH, wherein QCOOH is selected from natural chiral organic acids, natural chiral organic acid derivatives, unnatural chiral organic acids, unnatural chiral organic acid derivatives, natural amino acid derivatives, and unnatural amino acid derivatives. In some embodiments of Formula 3 and/or 3a, R² is Q of a chiral acid QCOOH, wherein QCOOH is a chiral acid selected from the group consisting of camphanic acid, 2-pyrrolidone-5-carboxylic acid, naproxen, ibuprofen; tartaric acid, malic acid, lactic acid, 3-hydroxybutyric acid, mandelic acid or derivatives thereof. In other embodiments of Formula 3, the chiral auxiliary group is a chiral alkoxyl and chiral aralkoxyl groups such as the menthoxy, and camphanoxy groups. In some embodiments of Formula 3 and/or 3a, R² is one of the following two groups:

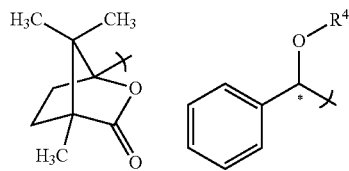

wherein R⁴ is a hydroxyl protecting group, and the carbon centre designated "*" is enantiomerically enriched in a (R)- or (S)-configuration.

R¹ of the compound of Formula 5 is necessarily related to the R² group of the precursor compound of Formulas 3, 3a or mixtures thereof. Generally, R¹ and R² will be the same for any given reaction of this sort. Hence, R¹ is as defined for R² in reactions where the compound of Formula 5 is generated from the compound of Formula 3, 3a or mixtures thereof.

The leaving group G may be independently selected from the group consisting of: halogen atoms (e.g. chlorine, bromine and iodine) and sulfonyloxy groups (e.g. methanesulfonyloxy, trifluoromethanesulfonyloxy, p-toluenesulfonyloxy). In some embodiments, G is chlorine.

The chiral acylating agent of Formula R²COG may be (−)-camphanic acid, (−)-camphanoyl chloride or (R)-2-chloro-2-oxo-1-phenethyl pivalate.

The reaction of a compound of Formula 2 and a chiral acylating agent may occur in the presence of a third base or an acid catalyst and typically in the second solvent as described above.

The metal may be a salt of a divalent cation, such as $Zn^{2+}$ or $Mg^{2+}$, or a monovalent cation, such as $Li^+$, $Na^+$ or $K^+$. The cyclopropyl acetylide metal reagent may be prepared in situ from the reaction of cyclopropyl acetylene and an organometallic compound. The organometallic compound may be selected from the group consisting of organomagnesium, organozinc, organosodium, organolithium compounds and mixtures thereof. The organometallic compound may be selected from the group consisting of alkylmagnesium halide, alkylzinc halide, alkyllithium, lithium hexaalkyldisilazide, sodium hexaalkyldisilazide, and potassium hexaalkyldisilazide. The organometallic compound may be selected from the group consisting of ethylmagnesium chloride, methylmagnesium chloride, n-butyllithium, sec-butyllithium, tert-butyllithium, n-hexyllithium and lithium hexamelthyldisilazide.

The reaction of the compound of Formula 3 and/or 3a with the compound of Formula 4 may be done in the presence of a third solvent. The third solvent may be an aprotic solvent. The third solvent may be an alkyl ether. The third solvent may be tetrahydrofuran.

The reaction may be done at a temperature range between about −78° C. to about 30° C.

Hydrolysis of the compound of Formula 5 to the compound of Formula 8 may be performed under acidic or basic conditions.

The cyclization of the compound of Formula 8 to give the compound of Formula 1 may be performed with a cyclization reagent. The cyclization reagent may be selected from the group consisting of alkyl haloformates, aryl haloformates, phosgene, triphosgene and 1,1'-carbonyldiimidazole.

EXAMPLES

The following examples are illustrative of some of the embodiments of the invention described herein. These examples should not be considered to limit the spirit or scope of the invention in any way.

Example 1

Preparation of 1-(2-amino-5-chlorophenyl)-2,2,2-trifluoroethanone (2)

A solution of 1-(2-amino-5-chlorophenyl)-2,2,2-trifluoroethanone hydrochloride hydrate (48.5 g, 174.4 mmol), 300 mL toluene, and 150 mL water was stirred at room temperature for 30 minutes. The pH of the solution was adjusted to 7-8 via the addition of saturated aqueous $NaHCO_3$ solution. The resulting mixture was then separated, and the toluene layer was collected and evaporated to dryness to give 38.2 g 1-(2-amino-5-chlorophenyl)-2,2,2-trifluoroethanone (2) as a yellow solid.

Example 2

Preparation of (1S,4R)-N-(4-chloro-2-(2,2,2-trifluoroacetyl)phenyl)-4,7,7-trimethyl-3-oxo-2-oxabicyclo[2.2.1]heptane-1-carboxamide (9)

A solution of 1-(2-amino-5-chlorophenyl)-2,2,2-trifluoroethanone (2, 5.0 g, 22.4 mmol), (−)-camphanoyl chloride (7.35 g, 33.9 mmol), and 50 mL dichloromethane was stirred at room temperature. Triethylamine (1.0 mL, 7.19 mmol, 0.3 eq) was added dropwise. The reaction mixture was stirred overnight at room temperature. The resulting suspension was treated with 10% critic acid aqueous, washed with water and brine. The organic layer was separated and evaporated to dryness to give 8.05 g (1S,4R)-N-(4-chloro-2-(2,2,2-trifluoroacetyl)phenyl)-4,7,7-trimethyl-3-oxo-2-ox abicyclo[2.2.1]heptane-1-carboxamide (9). $^1$H NMR (CDCl$_3$) δ 11.48 (s, 1H), 8.81 (d, J=9.1 Hz, 1H), 7.94 (s, 1H), 7.68 (ad, J=9.1 Hz, 1H), 2.64-2.54 (m, 1H), 2.09-1.96 (m, 2H), 1.82-1.73 (m, 1H), 1.17 (s, 3H), 1.15 (s, 3H), 0.99 (s, 3H).

Example 3

Preparation of (R)-2-chloro-2-oxo-1-phenylethyl pivalate (R)-Mandelic acid (10 g, 65.7 mmol) was dissolved in toluene (20 mL) at which point pivaloyl chloride (10.2 mL, 82.9 mmol) was added. This mixture was stirred at 60° C. for 3 hours. After cooling the reaction mixture to 30° C., toluene (10 mL), N,N-dimethylformamide (0.3 mL) and thionyl chloride (10 mL) were added. The reaction mixture was stirred at 35° C. for 2 hours and then at 50° C. for 4 hours. Then the mixture was evaporated to dryness to furnish 14.5 g (R)-2-chloro-2-oxo-1-phenylethyl pivalate as a yellow oil.

Example 4

Preparation of (R)-2-(4-chloro-2-(2,2,2-trifluoroacetyl)-phenylamino)-2-oxo-1-phenylethyl pivalate (12)

1-(2-amino-5-chlorophenyl)-2,2,2-trifluoroethanone (2, 5.0 g, 22.4 mmol) was dissolved in dichloromethane (50 mL) and (R)-2-chloro-2-oxo-1-phenylethyl pivalate (8.54 g, 33.5 mmol) was added. To this mixture N,N-dimethylaniline (2.8 mL, 22.4 mmol) was added. The reaction mixture was stirred at room temperature for 3 hours. The mixture was diluted with dichloromethane (50 mL), treated with 1N HCl, washed with brine and the organic layer was separated and evaporated to give (R)-2-(4-chloro-2-(2,2,2-trifluoroacetyl)-phenylamino)-2-oxo-1-phenylethyl pivalate (12) as an brown oil.

Example 5

Preparation of (1S,4R)-N-(4-chloro-2-((S)-4-cyclopropyl-1,1,1-trifluoro-2-hydroxybut 3-yn-2-yl)phenyl)-4,7,7-trimethyl-3-oxo-2-oxabicyclo[2.2.1]heptane-1-carboxamide (10)

Ethylmagnesium bromide 3M in ether (5.98 mL, 17.95 mmol) was added slowly to a solution of cyclopropyl acetylene (1.19 g, 17.95 mmol) in tetrahydrofuran (18 mL) in an ice-bath under argon and the mixture was stirred at 40° C. for 3 hours. Then (1S,4R)-N-(4-chloro-2-(2,2,2-trifluoroacetyl)phenyl)-4,7,7-trimethyl-3-oxo-2-oxabicyclo[2.2.1]heptane-1-carboxamide (9, 1.45 g, 3.59 mmol) was added in portions while the flask was in an ice-bath. The reaction mixture was stirred at room temperature for 2 hours. The reaction was quenched with saturated aqueous NH$_4$Cl, and the mixture was extracted with ethyl acetate and two layers were separated. The organic layer was evaporated to dryness to give 1.67 g of the compound as a crude oil. It was further crystallized with petroleum ether and ethyl acetate to furnish (1S,4R)-N-(4-chloro-2-((S)-4-cyclopropyl-1,1,1-trifluoro-2-hydroxybut 3-yn-2-yl)phenyl)-4,7,7-trimethyl-3-oxo-2-oxabicyclo[2.2.1]heptane-1-carboxamide (10) as a white or off-white solid. This solid was shown to be 98.8% de by HPLC.

$^1$H NMR (CDCl$_3$) δ 10.52 (s, 1H), 8.42 (d, J=8.9 Hz, 1H), 7.72 (s, 1H), 7.35 (ad, J=8.9 Hz, 1H), 5.05 (s, 1H), 2.68-2.56 (m, 1H), 2.03-1.93 (m, 2H), 1.74-1.65 (m, 1H), 1.44-1.35 (m, 1H), 1.14 (s, 3H), 1.13 (s, 3H), 0.95 (s, 3H), 0.90-0.87 (m, 2H), 0.80-0.77 (m, 2H).

Example 6

Preparation of (1S,4R)-N-(4-chloro-2-((S)-4-cyclopropyl-1,1,1-trifluoro-2-hydroxybut 3-yn-2-yl)phenyl)-4,7,7-trimethyl-3-oxo-2-oxabicyclo[2.2.1]heptane-1-carboxamide (10)

2.5 M n-Butyllithium (14.8 mL, 37.16 mmol) was added slowly to a solution of cyclopropyl acetylene (2.46 g, 37.16 mmol) in tetrahydrofuran (20 mL) in an ice-salt-bath under argon, and then (1S,4R)-N-(4-chloro-2-(2,2,2-trifluoroacetyl)phenyl)-4,7,7-trimethyl-3-oxo-2-oxabicyclo[2.2.1]heptane-1-carboxamide(9, 5 g, 12.39 mmol) was added. The reaction mixture was stirred for 0.5 hour. The reaction was quenched with 10% citric acid aqueous, the mixture was extracted with ethyl acetate and the two layers were separated. The organic layer was evaporated to dryness to give crude oil which was further crystallized with ethyl acetate and petroleum ether to give (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10) as a white or off-white powder. $^1$H NMR spectrum of the product was identical to that of Example 5.

Example 7

Preparation of (1S,4R)-N-(4-chloro-2-((S)-4-cyclopropyl-1,1,1-trifluoro-2-hydroxybut 3-yn-2-yl)phenyl)-4,7,7-trimethyl-3-oxo-2-oxabicyclo[2.2.1]heptane-1-carboxamide (10)

1M LiHMDS (7.4 mL, 7.4 mmol) was added slowly to a solution of cyclopropyl acetylene (0.49 g, 7.4 mmol) in THF (4 mL) in an ice-salt bath under argon, and then (1S, 4R)-N-(4-chloro-2-(2,2,2-trifluoroacetyl)phenyl)-4,7,7-trimethyl-3-oxo-2-oxabicyclo[2.2.1]heptane-1-carboxamide (9, 1 g., 2.48 mmol) in THF (1.5 mL) was added slowly. The mixture was stirred at −15° C. for 20 minutes. TLC showed the formation of the product. The reaction mixture was worked up similarly to the example 6, and (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10) was isolated as an off-white solid. $^1$H NMR spectrum of the product was identical to that of Example 5.

Example 8

Preparation of (R)-2-(4-chloro-2-((S)-4-cyclopropyl-1,1,1-trifluoro-2-hydroxybut-3-yn-2-yl)phenylamino)-2-oxo-1-phenylethyl pivalate (13)

Ethylmagnesium bromide 3 M in ether (2 mL, 6.2 mmol) was added slowly to a solution of cyclopropyl acetylene (0.41 g, 6.2 mmol) in THF (5 mL) in an ice-bath under argon. The mixture was stirred at 0° C. for 1 hour and then 40° C. for 2 hours. Then (R)-2-(4-chloro-2-(2,2,2-trifluoroacetyl)phenylamino)-2-oxo-1-phenylethyl pivalate (12, 0.55 g, 1.24 mmol) in THF (2 mL) was added slowly in an ice-bath. The mixture was stirred at 0° C. for 1.5 hours. 10% Citric acid was added to quench the reaction. The organic layer was washed with water and then evaporated to dryness to give (R)-2-(4- chloro-2-((S)-4-cyclopropyl-1,1,1-trifluoro-2-hydroxybut-3-yn-2-yl)phenylamino)-2-oxo-1-phenylethyl pivalate (13). This solid was shown to be 35.9% de by chiral HPLC. The pure product was isolated by chromatography.

Example 9

Preparation of 6-chloro-4-(cyclopropylethynyl)-4-(trifluoromethyl)-1H-benzo[d][1,3]oxazin-2(4H)-one (racemic Efavirenz)

A solution of N-(4-chloro-2-(4-cyclopropyl-1,1,1-trifluoro-2-hydroxybut-3-yn-2-yl)phenyl)acetamide (5, $R^1$ is methyl, 1.1 g, 3.3 mmol), toluene (5.5 mL) and triethylamine (0.5 mL, 3.65 mmol) was stirred at 0-5° C. under nitrogen then 1-chloroethyl chloroformate (0.52 g, 3.65 mmol) was added dropwise. The mixture was stirred at 5-10° C. overnight. Water (20 mL) was added and the mixture was separated. The organic layer was evaporated to dryness whereupon N,N-dimethyl formamide (5 mL) and $K_2CO_3$ (0.9 g, 6.6 mmol) were added. The reaction mixture was stirred at room temperature for 1 day. Toluene (20 mL) and water (20 mL) were added to the mixture, and the resulting mixture was separated. The organic layer was washed with water (20 mL), and evaporated to dryness to give 6-chloro-4-(cyclopropylethynyl)-4-(trifluoromethyl)-1H-benzo[d][1,3]oxazin-2 (4H)-one as an off-white solid. $^1$H NMR (CDCl$_3$) δ 9.64 (s, 1H), 7.49 (a, s, 1H), 7.36 (dd, J=8.4, 1.8 Hz, 1H), 6.87 (d, J=8.4 Hz, 1H), 1.43-1.36 (m, 1H), 0.97-0.91 (m, 2H), 0.88-0.86 (m, 2H), Example 10

Preparation of (S)-6-chloro-4-(cyclo propylethynyl)-4-(trifluoromethyl)-1H-benzo[d][1,3]oxazin-2(4H)-one (Efavirenz, 1

A solution of (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10, 5.0 g, 10.6 mmol), methyl tert-butyl ether (30 mL), 1 N NaOH aqueous (25 mL), and 4-nitrophenyl chloroformate (2.8 g, 13.8 mmol) was stirred at room temperature for 10 minutes. Then two layers were separated and NaOH (2.1 g, 52.5 mmol) was added to the organic layer. The mixture was stirred for 1 hour. The suspension was filtered and rinsed with methyl tert-butyl ether (3×10 mL), then the filtrate was washed with 1 N NaOH (25 mL), water (25 mL), and the two layers were separated. The organic layer was evaporated to about 10 mL, heptanes (25 mL) was added. Then the mixture was stirred at room temperature for an hour, the resulting suspension was filtered and washed with heptanes to give 1.5 g (S)-6-chloro-4-(cyclopropylethynyl)-4-(trifluoromethyl)-1,4-dihydro-2H-3,1-benzoxazin-2-one (Efavirenz, 1) as a white or off-white solid.

Example 11

Preparation of (S)-2-(5-chloro-2-((1S, 4R)-4,7,7-trimethyl-3-oxo-2-oxabicyclo[2.2.1]heptane-1-carboxamido)phenyl)-4-cyclopropyl-1,1,1-trifluorobut-3-yn-2-yl 1-chloroethyl carbonate (7, $R^1$ is 4,7,7-trimethyl-3-oxo-2-oxabicyclo[2.2.1]heptyl, $R^3$ is 1-chloroethyl)

A solution of (1S,4R)-N-(4-chloro-2-((S)-4-cyclopropyl-1,1,1-trifluoro-2-hydroxybut-3-yn-2-yl) phenyl)-4,7,7-trimethyl-3-oxo-2-oxabicyclo[2.2.1]heptane-1-carboxamide (10, 20 g, 42.6 mmol), dichloromethane (100 mL) and triethylamine (5.17 g, 51.1 mmol) was stirred at 0-5° C. for 20 minutes, then 1-chloroethyl chloroformate (7.3 g, 51.1 mmol) was added dropwise. The mixture was stirred at 5-10° C. for 1 hour. Water (60 ml) was added with stirring and then the layers were separated. The organic solution was concentrated and MTBE (180 ml) was added. After washing with water twice, the system was concentrated to 30 ml and then MTBE (10 ml) and hexane (60 ml) were added. The suspension was stirred at 70° C. for 30 min and filtered to give (S)-2-(5-chloro-2-((1S,4R)-4,7,7-trimethyl-3-oxo-2-oxabicyclo[2.2.1]heptane-1-carboxamido)phenyl)-4-cyclopropyl-1,1,1-trifluorobut-3-yn-2-yl 1-chloroethyl carbonate (7, $R^1$ is 4,7,7-trimethyl-3-oxo-2-oxabicyclo[2.2.1]heptyl, $R^3$ is 1-chloroethyl) as a white solid. $^1$H NMR (CDCl$_3$) δ9.43, 9.30 (s, 1H), 8.17, 8.06 (d, J=8.7 Hz, 1H), 7.62, 7.54 (s, 1H), 7.42 (d, J=8.7 Hz, 1H), 6.36 (q, J=5.7 Hz, 1H), 2.60-2.50 (m, 1H), 2.09-1.93 (m, 2H), 1.89-1.86 (at, J=4.5 Hz, 3H), 1.77-1.61 (m, 2H), 1.16 (d, J=10.5 Hz, 6H), 1.01 (d, J=7.5 Hz, 3H), 0.97-0.92 (m, 2H), 0.88-0.84 (m, 2H).

Example 12

Preparation of (S)-6-chloro-4-(cyclopropylethynyl)-4-(trifluoromethyl)-1,4-dihydro-2H-3,1-benzoxazin-2-one (Efavirenz, 1)

$K_2CO_3$ (13.3 g, 95.8 mmol) powder was added to a solution of (S)-2-(5-chloro-2-((1S,4R)-4,7,7-trimethyl-3-oxo-2-oxabicyclo[2.2.1]heptane-1-carboxamido) phenyl)-4-cyclopropyl-1,1,1-trifluorobut-3-yn-2-yl 1-chloroethyl carbonate (7, $R^1$ is 4,7,7-trimethyl-3-oxo-2-oxabicyclo[2.2.1]heptyl, $R^3$ is 1-chloroethyl, 36.8 g, 63.9 mmol) in N,N-dimethylformamide (150 mL). The reaction mixture was stirred at room temperature overnight. Methyl t-butyl ether (300 mL) and water (300 mL) were added to the mixture, and the resulting layers were separated. The organic layer was washed with brine and evaporated to 60 mL then petroleum ether (200 mL) was added. The resulting mixture was filtered and rinsed with petroleum ether to give (S)-6-chloro-4-(cyclopropylethynyl)-4-(trifluoromethyl)-1,4-dihydro-2H-3,1-benzoxazin-2-one (Efavirenz, 1) as an off-white solid.

Example 13

Preparation of (S)-6-chloro-4-(cyclo propylethynyl)-4-(trifluoromethyl)-1H-benzo[d][1,3]oxazin-2(4H)-one (Efavirenz, 1)

A solution of (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10, 30 g, 63.9 mmol), dichloromethane (150 mL) and triethylamine (7.11 g, 70.2 mmol) was stirred at 0-5° C. for 20 minutes, then 1-chloroethyl chloroformate (10.0 g, 70.2 mmol) was added dropwise. The mixture was stirred at 5-10° C. for 1 hour. Then N,N-dimethylformamide (150 mL) was added and further evaporated to 220 mL, then $K_2CO_3$ (13.3 g, 95.8 mmol) was added. The reaction mixture was stirred at room temperature overnight. Methyl t-butyl ether (300 mL) and water (200 mL) were added to the mixture, and the resulting layers were separated. The organic layer was washed with brine, and concentrated to 60 mL whereupon petroleum ether (200 mL) was added and stirred. The resulting precipitate was filtered and rinsed with petroleum ether to provide 18.4 g (S)-6-chloro-4-(cyclopropylethynyl)-4-(trifluoromethyl)-1,4-dihydro-2H-3,1-benzoxazin-2-one (Efavirenz, 1) as an off-white solid.

Example 14

Preparation of (S)-4-chloro-2-(4-cyclopropyl-1,1,1-trifluoro-2-hydroxybut-3-yn-2-yl) aniline (8)

A suspension of (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10, 1 g, 2.13 mmol) and 40% NaOH aqueous solution (20 mL) was stirred at 90-95° C. for 20 hours. Toluene (20 mL) was added and the layers were separated. The organic layer was washed with water (20 mL) and evaporated to dryness to give (S)-4-chloro-2-(4-cyclopropyl-1,1,1-trifluoro-2-hydroxybut-3-yn-2-yl) aniline (8).
$^1$H NMR (CDCl$_3$) δ 7.54 (s, 1H), 7.12 (dd, J=8.5, 1.5 Hz, 1H), 6.62 (d, J=8.6 Hz, 1H), 4.47 (br. s, 3H), 1.44-1.35 (m, 1H), 0.93-0.88 (m, 2H), 0.83-0.80 (m, 2H).

Example 15

Preparation of (S)-6-chloro-4-(cyclopropylethynyl)-4-(trifluoromethyl)-1,4-dihydro-2H-3,1-benzoxazin-2-one (Efavirenz, 1)

A solution of (S)-4-chloro-2-(4-cyclopropyl-1,1,1-trifluoro-2-hydroxybut-3-yn-2-yl)aniline (4.42 g, 15.3 mmol), 1,1'-carbonyl diimidazole and toluene (50 mL) was stirred at room temperature for 10 minutes. The reaction was quenched with ice-water (10 mL). The two layers were separated, ethyl acetate (10 mL) was added to the toluene layer and the mixture was washed with brine (2×30 mL) and the two layers were separated. The organic layer was evaporated to dryness to give an orange oil and further crystallized with hexanes to give (S)-6-chloro-4-(cyclopropylethynyl)-4-(trifluoromethyl)-1,4-dihydro-2H-3,1-benzoxazin-2-one as a white or off-white solid. $^1$H NMR (CDCl$_3$) δ 9.64 (s, 1H), 7.49 (a, s, 1H), 7.36 (dd, J=8.4, 1.8 Hz, 1H), 6.87 (d, J=8.4 Hz, 1H), 1.43-1.36 (m, 1H), 0.97-0.91 (m, 2H), 0.88-0.86 (m, 2H).

Example 16

Preparation of N,N-bis((1S,4R)-4,7,7-trimethyl-3-oxo-2-oxabicyclo[2.2.1]heptane-1-carbonyl)-4-chloro-2-(2,2,2-trifluoroacetyl)aniline (11)

A solution of 1-(2-amino-5-chlorophenyl)-2,2,2-trifluoroethanone (2, 40 g, 0.179 mol), (−)-camphanoyl chloride (116 g, 0.537 mol), toluene (120 mL), and dichloromethane (100 mL) was stirred at room temperature. Triethylamine (125 mL, 0.895 mol, 5 eq) was added dropwise. The reaction mixture was stirred at room temperature for 1 day. The resulting suspension was treated with 1N HCl and washed with water and brine. The organic layer was separated and evaporated to dryness to provide N,N-bis((1S,4R)-4,7,7-trimethyl-3-oxo-2-oxabicyclo[2.2.1]heptane-1-carbonyl)-4-chloro-2-(2,2,2-trifluoroacetyl)aniline (11).

Example 17

Preparation of (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10)

2.5M n-Butyllithium (2.05 mL, 5.14 mmol) was added slowly to a solution of cyclopropyl acetylene (0.34 g, 5.14 mmol) in tetrahydrofuran (4 mL) in an ice-salt-bath under argon, and then N,N-bis((1S,4R)-4,7,7-trimethyl-3-oxo-2-oxabicyclo[2.2.1]heptane-1-carbonyl)-4-chloro-2-(2,2,2-trifluoroacetyl)aniline (11, 1 g, 1.71 mmol) in THF (2 mL) was added. The reaction mixture was stirred for 1 hour. The reaction was quenched with 10% citric acid aqueous, the mixture was extracted with ethyl acetate and the two layers were separated. The organic layer was evaporated to dryness to give a crude oil and further crystallized with ethyl acetate and petroleum ether to give pure (1S,4R)-N-(4-chloro-2-((S)-4-cyclopropyl-1,1,1-trifluoro-2-hydroxybut-3-yn-2-yl)phenyl)-4,7,7-trimethyl-3-oxo-2-oxabicyclo[2.2.1]heptane-1-carboxamide (10).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A compound of Formula 3:

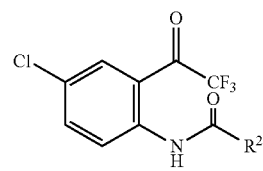

wherein
R$^2$ is a chiral auxiliary group.

2. The compound of claim 1 wherein the chiral auxiliary group is Q of a chiral acid QCOOH, wherein QCOOH is selected from the group consisting of:
natural chiral organic acids, unnatural chiral organic acids, natural amino acid, and unnatural amino acid.

3. The compound of claim 1 wherein the chiral auxiliary group is a chiral C$_4$-C$_{10}$ alkoxyl or a chiral C$_6$-C$_{12}$ aralkoxyl group.

4. The compound of claim 1 wherein the chiral auxiliary group is Q of a chiral acid QCOOH, wherein QCOOH is selected from the group consisting of: camphanic acid, 2-pyrrolidone-5-carboxylic acid, naproxen, ibuprofen; tartaric acid, malic acid, lactic acid, 3-hydroxybutyric acid, and mandelic acid.

5. The compound of claim 1 wherein $R^2$ is
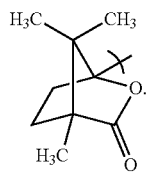
6. The compound of claim 1 wherein $R^2$ is
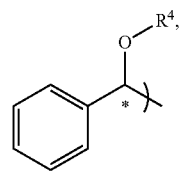
wherein $R^4$ is a hydroxyl protecting group and the carbon centre designated "*" is enantiomerically enriched in a (R)- or (S)-configuration.
7. The compound of claim 1 wherein $R^2$ is
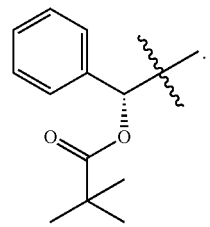 [SMILES: *[C@H](OC(=O)C(C)(C)C)c1ccccc1]
* * * * *